United States Patent
Rezachek et al.

(10) Patent No.: US 9,086,364 B2
(45) Date of Patent: *Jul. 21, 2015

(54) PHOTOACOUSTIC SENSOR WITH BASELINE AND SPAN CORRECTION

(75) Inventors: Thomas M. Rezachek, Cottage Grove, MN (US); Gary Shubinsky, Buffalo Grove, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1083 days.

This patent is subject to a terminal disclaimer.

(21) Appl. No.: 13/096,940

(22) Filed: Apr. 28, 2011

(65) Prior Publication Data

US 2012/0272718 A1 Nov. 1, 2012

(51) Int. Cl.
*G01N 21/00* (2006.01)
*G01N 21/17* (2006.01)

(52) U.S. Cl.
CPC .... *G01N 21/1702* (2013.01); *G01N 2021/1704* (2013.01)

(58) Field of Classification Search
CPC .............. G01N 21/1702; G01N 2021/1704; G01N 21/3504; G01N 21/274; G01N 33/0006; G01N 2201/127
USPC ........... 324/612–619; 73/24.02, 24.01, 24.06, 73/1.01, 1.02, 1.03, 1.06; 356/932, 450, 356/437
See application file for complete search history.

(56) References Cited

U.S. PATENT DOCUMENTS

| | | | |
|---|---|---|---|
| 6,843,102 B1* | 1/2005 | Shulga et al. | 73/25.01 |
| 8,689,607 B2* | 4/2014 | Rezachek et al. | 73/24.02 |
| 2003/0112019 A1* | 6/2003 | Forster et al. | 324/633 |
| 2005/0121614 A1 | 6/2005 | Stuttard | 250/343 |
| 2006/0290944 A1* | 12/2006 | Arnott et al. | 356/519 |
| 2009/0320561 A1 | 12/2009 | Fritz et al. | 73/24.02 |
| 2010/0027012 A1 | 2/2010 | Fritz et al. | 356/432 |
| 2010/0045998 A1 | 2/2010 | Fritz et al. | 356/450 |
| 2010/0147051 A1 | 6/2010 | Tobias | 73/24.02 |
| 2012/0279279 A1* | 11/2012 | Rezachek et al. | 73/24.02 |

* cited by examiner

*Primary Examiner* — Daniel S Larkin
*Assistant Examiner* — Jamar Ray
(74) *Attorney, Agent, or Firm* — Husch Blackwell LLP

(57) ABSTRACT

A photoacoustic detector wherein a detector response transfer function can be measured at various times under predetermined conditions during the life of the detector. One or more of the time related transfer functions each can, when acquired, be compared to the stored initial transfer function established at initial manufacture and calibration of the detector. Span and baseline correction values can be determined. These values can be used to compensate detected output values during normal operation. Time related transfer functions can be compared to each other as well as to the stored initial transfer function.

11 Claims, 2 Drawing Sheets

PHOTOACOUSTIC SENSOR WITH BASELINE AND SPAN CORRECTION

FIELD

The application pertains to photoacoustic detectors. More particularly, the application pertains to such detectors which include circuitry for carrying out baseline and span correction.

BACKGROUND

Various types of photoacoustic sensors are known to detect gases. These include, Fritz et al., US Patent Application No. 2009/0320561, published Dec. 31, 2009 and entitled "Photoacoustic Cell"; Fritz et al., US Patent Application No. 2010/0027012, published Feb. 4, 2010 and entitled, "Photoacoustic Spectroscopy System"; Fritz et al., US Patent Application No. 2010/0045998, published Feb. 25, 2010 and entitled "Photoacoustic Sensor". The above noted published applications have been assigned to the assignee hereof, and are incorporated herein by reference.

Precise and repeatable performance of photoacoustic detectors is preferred. Changes in detector response over a period of time can result in measurements exhibiting variances from those initially determined during manufacture and initial calibration. In some instances this can result in the respective detector drifting out of specification.

DETAILED DESCRIPTION

Figure 1:
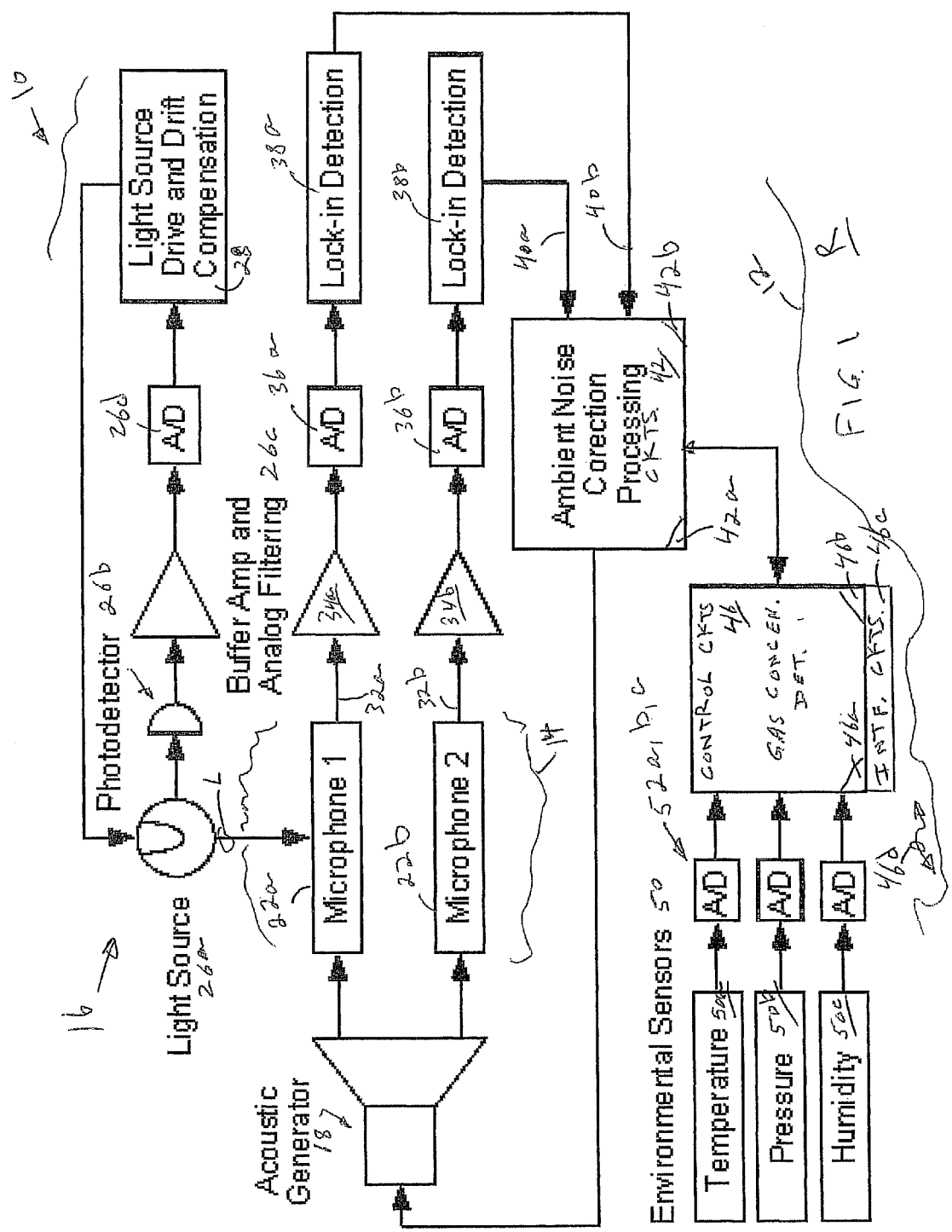
FIG. 1 is a block diagram of an embodiment hereof.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

A disclosed embodiment utilizes an infra-red source of radiant energy. The radiant energy is then injected into a photoacoustic sensing chamber or cell. As those of skill in the art would understand, source output can be varied between multiple intensity values while sensing and measuring a photoacoustic output signal.

An initial transfer function for the cell and associated circuitry can be established and stored. This process can involve a fully assembled detector, or a partially assembled unit, all without limitation.

A detector response transfer function can be measured at various times under predetermined conditions during the life of the detector. One or more of the time related transfer functions each can, when acquired, be compared to the stored initial transfer function established at initial manufacture and calibration of the detector. Span and baseline correction values can be determined. These values can be used to compensate detected output values during normal operation. Time related transfer functions can be compared to each other as well as to the stored initial transfer function.

Radiant energy intensity variations can be measured using a photo sensor in a closed loop control system. Unlike known compensation methods, which require a known gas concentration, the present method only requires that the gas concentration not change substantially during the time of calibration.

FIG. 1 is a block diagram of an exemplary detector 10 in accordance herewith. It will be understood that the detector 10 is exemplary only. Other detectors come within the spirit and scope hereof.

The detector 10 can monitor concentrations of one or more airborne gases in an adjacent region R. Detector 10 includes a housing 12 which can carry a photoacoustic sensing chamber or cell 14.

Detector 10 includes a radiant energy emitting and control system 16 and an acoustic generator 18. Dual microphones 22 $a$, $b$ are carried by or adjacent to the chamber 14 and respond to inputs from generator 18. The microphones 22 $a$, $b$ also respond to audio generated by radiant energy, or light L, from a source 26$a$.

The source 26$a$ injects light into the chamber 14 as would be understood by those of skill in the art to produce a photoacoustic audio signal, and need not be discussed further. The source 26$a$ can emit infra-red radiant energy.

Feedback is provided in system 16 by a photodetector 26$b$ which couples a signal, indicative of the output of source 26$a$ through an amplifier and filter 26$c$, via an analog-to-digital converter 26$d$ to drive and drift compensation circuits 28.

Dual channel output signals on lines 32 $a$, $b$ from the microphones 22 $a$, $b$ can be coupled via amplifiers 34 $a$, $b$ to analog-to-digital converters 36 $a$, $b$ to lock-in detection circuits 38 $a$, $b$. Output signals on lines 40 $a$, $b$ from the detection circuits 38 $a$, $b$ can be coupled to ambient noise correction processing circuits 42. Processing circuits 42 can be implemented with one or more programmable processors 42$a$ which execute software or control programs 42$b$ pre-stored on computer readable media such as semiconductor memory chips.

The corrected outputs can be coupled to control and processing circuits 46 which can carry out gas concentration detection. Circuits 46 can be implemented with one or more programmable processors 46$a$ which execute software or control programs 46$b$ pre-stored on computer readable media such as semiconductor memory chips. Using pre-stored instructions, such as 42$b$, baseline and span corrections can be carried out as explained below.

Interface circuits 46$c$, also coupled to the control circuits 46 provide for bidirectional communication with a docking station, or, a displaced monitoring system via a wired or wireless medium 46$d$. Environmental sensors 50$a$, $b$, $c$ can detect ambient temperature, pressure or humidity in the vicinity of the housing 12. Signals from the sensors 50$a$, $b$, $c$ can be digitized in analog-to-digital converters 52$a$, $b$, $c$ and the coupled to the control circuits 46 as discussed above.

Further, closed loop control system 16, which can include the infra-red emitter of radiant energy, source 26$a$, can sense emitted radiant energy intensity, or amplitude, via detector 26$b$. The system 16 compensates for drift in output of the radiant energy source 26$a$.

The detector 10 can be calibrated at manufacture. A detector response transfer function can be established at initial calibration. Characteristics of the initial transfer function can be stored by control circuits 46 for subsequent use.

Subsequently, in one embodiment, the intensity of the infra-red source 26$a$ can be varied while measuring the cell output signal. An updated transfer function can be established and compared to the stored transfer function. Span and baseline correction values can be determined using the original and current transfer functions. The correction values can also be stored by control circuits 46 for subsequent use in compensating gas concentration values.

Figure 2:
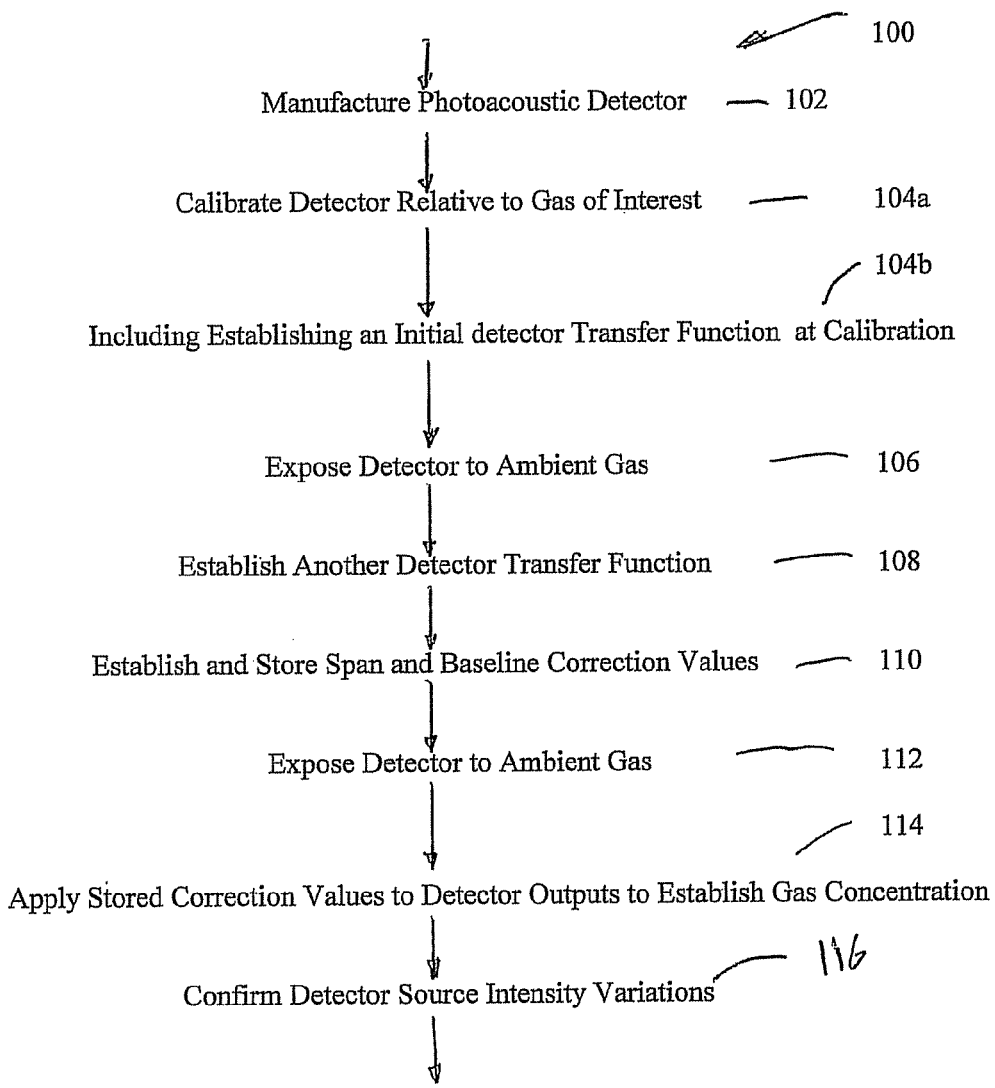
FIG. 2 is a flow diagram of a compensation method.

FIG. 2 is a flow diagram of one embodiment of a method 100 in accordance herewith. A detector can be manufactured, as at 102. The detector can be calibrated, relative to a gas of interest, as at 104a. Calibration can include establishing an initial detector transfer function 104b.

The detector can then be exposed to ambient gases as at 106. Another detector transfer function can be established as at 108.

Span and baseline correction values can be established and stored using at least two transfer functions, as at 110.

The detector can again be exposed to ambient gases as at 112. The stored correction values can be applied to detector outputs to establish a gas concentration as at 114. Finally, detector source intensity variations can be confirmed, as at 116.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacostic detector comprising:
a sensing chamber;
control circuits coupled to the sensing chamber, the control circuits include a pre-stored representation of a detector transfer function indicative of detector performance wherein the detector transfer function is measured by varying a source of radiant energy injected into the sensing chamber between multiple intensity values while sensing and measuring a photoacoustic output wherein the pre-stored representation of the detector transfer function is compared to a current transfer function, and, which includes circuitry to determine at least one compensation value;
circuitry to combine at least one compensation value with at least one current indicator of gas concentration;
at least one acoustic transducer carried adjacent to the chamber where the control circuits are coupled to the transducer, where the control circuits receive a first electrical signal from the transducer and including processing circuits, which, over a predetermined time interval, process the first electrical signal from the transducer to increase the signal-to-noise ratio thereof;
a second acoustic transducer carried adjacent to the chamber and where the processing circuits process a second electrical signal, from the second acoustic transducer and
confirmation circuitry to determine that first and second ambient-noise corrected signals, obtained from the first and second electrical signals, exhibit a constant amplitude ratio and a fixed phase relationship, and which responsive thereto, generates an indicium indicative thereof.

2. A detector as in claim 1 which includes a closed loop radiant energy control system.

3. A detector as in claim 2 where the closed loop radiant energy control system includes an infra-red emitter oriented to direct infra-red radiant energy into the sensing chamber and an optical sensor to provide feedback.

4. A detector as in claim 1 which includes additional circuitry to eliminate a noise component from the processed signals.

5. A photoacostic detector comprising:
a sensing chamber;
control circuits coupled to the sensing chamber, the control circuits include a pre-stored representation of a detector transfer function indicative of detector performance wherein the detector transfer function is measured by varying a source of radiant energy injected into the sensing chamber between multiple intensity values while sensing and measuring a photoacoustic output;
first and second acoustic transducers carried adjacent to the chamber where the control circuits are coupled to the first and second transducers, where the control circuits receive a first electrical signal from the first transducer and a second signal from the second transducer;
circuitry that applies stored correction values of the pre-stored representation to the respective first and second processed electrical signals; and
confirmation circuitry to determine that the first and second electrical signals corrected by the stored correction values, exhibit a constant amplitude ratio and a fixed phase relationship, and which responsive thereto, generates an indicium indicative thereof.

6. A detector as in claim 5 further comprising processing circuits, which, over a predetermined time interval, process the respective first and second electrical signals from the transducers to increase the signal-to-noise ratio thereof.

7. A detector as in claim 5 wherein the pre-stored representation of the transfer function is compared to a current transfer function, and, which includes circuitry to determine at least one compensation value.

8. A detector as in claim 7 which includes circuitry to combine at least one compensation value with at least one current indicator of gas concentration.

9. A detector as in claim 8 which includes a closed loop radiant energy control system.

10. A detector as in claim 9 where the closed loop radiant energy control system includes an infra-red emitter oriented to direct infra-red radiant energy into the sensing chamber and an optical sensor to provide feedback.

11. A photoacostic detector comprising:
a sensing chamber;
control circuits coupled to the sensing chamber, the control circuits include a pre-stored representation of a detector transfer function indicative of detector performance wherein the detector transfer function is measured by varying a source of radiant energy injected into the sensing chamber between multiple intensity values while sensing and measuring a photoacoustic output;
first and second acoustic transducers carried adjacent to the chamber where the control circuits are coupled to the first and second transducers, where the control circuits receive a first electrical signal from the first transducer and a second signal from the second transducer and including processing circuits, which, over a predetermined time interval, process the respective first and second electrical signals from the transducers to increase the signal-to-noise ratio thereof;
circuitry that applies stored correction values of the pre-stored representation to the respective first and second processed electrical signals; and
confirmation circuitry to determine that first and second ambient-noise corrected signals, obtained from the first and second electrical signals and corrected by the stored correction values, exhibit a constant amplitude ratio and a fixed phase relationship, and which responsive thereto, generates an indicium indicative thereof.

* * * * *